United States Patent [19]

Heiman et al.

[11] Patent Number: 5,130,471

[45] Date of Patent: Jul. 14, 1992

[54] STABILIZED ACRYLIC MONOMER COMPOSITIONS

[76] Inventors: John C. Heiman, 14 Seminole La., West Columbia, Tex. 77486; Jerald W. Darlington, 132 Spruce, Lake Jackson, Tex. 77566

[21] Appl. No.: 756,099

[22] Filed: Sep. 6, 1991

[51] Int. Cl.$^5$ .............................. C07L 69/52
[52] U.S. Cl. ..................................... 560/205
[58] Field of Search ......................... 560/205

[56] References Cited

U.S. PATENT DOCUMENTS

| | | | |
|---|---|---|---|
| 4,059,721 | 11/1977 | Rosenkranz et al. | 560/205 |
| 4,117,241 | 9/1978 | Hudson | 560/205 |
| 4,754,058 | 6/1988 | Levy | 560/205 |

FOREIGN PATENT DOCUMENTS 1256428 12/1971 United Kingdom .

*Primary Examiner*—Paul J. Killos

[57] ABSTRACT

A stabilized acrylic monomer composition is provided in which polymerization of the monomer is inhibited during transport and storage as well as during the distillation process for purifying or separating the acrylic monomer. The compositions of the present invention comprise three components: an acrylic monomer (A), phenothiazine (B), and a cyclic amine having at least one hydroxyl group (C).

12 Claims, No Drawings

5,130,471

STABILIZED ACRYLIC MONOMER COMPOSITIONS

FIELD OF THE INVENTION

This invention relates to acrylic monomer compositions which are stabilized against the polymerization of the acrylic acid monomers. More specifically, the present invention relates to stabilized acrylic monomer compositions in which polymerization of the monomer is inhibited during transport and storage as well as during the distillation process for purifying or separating the acrylic monomer.

BACKGROUND OF THE INVENTION

In preparing acrylic acid or preparing acrylic esters from acrylic acid by either the esterification reaction or the transesterification reaction, a distillation operation for separating, concentrating or purifying is typically employed. It is known that acrylic acid and its esters have high polymerization tendency which becomes extremely high at elevated temperatures such as in the distillation step. Therefore, in the preparation of acrylic acid and its esters on a commercial scale, the prevention of polymerization during the distillation step is extremely important to the stable operation of the process.

When distilling acrylic acid or its esters in the separation, concentration or purification step, it is known that a polymer may be formed at various places, for example, in the reverse side of the trays, the inside of the bubble caps, the external surface of the downcomers and the recessed portions on the column wall which are not perpetually wetted with a liquid containing polymerization inhibitors, as well as the hardware (e.g., bolts, nuts), the packing and the gaskets for setting up the trays at which liquid tends to stagnate. The polymers thus formed do not readily dissolve in acrylic acid, acrylic esters, water or other organic solvents. Further, once the polymer forms inside the column, it becomes a nucleus of polymerization to cause a gradual accumulation of polymer which can block the inside of the column and render impossible the continuous distillation operation. Moreover, great difficulty is involved in removing this accumulated polymer.

Previously, as a measure to inhibit the polymerization of acrylic acid or esters thereof during their distillation, there was proposed in the specification of the German Laid-Open Pat. No. 2,027,655 a distillation column of a construction in which the reverse side of the trays and the inside wall of the column have been made readily wettable. Aside from this proposal, the method most widely used heretofore for inhibiting the polymerization of these compounds is that of adding a polymerization inhibitor to the distillation column.

Typical polymerization inhibitors are phenolic compounds, amine compounds, nitro compounds, quinone compounds and the inorganic salts.

Illustrative of the methods of using these polymerization inhibitors is U.S. Pat. No. 3,666,795 which uses the combination of hydroquinone-phenoloxygen and U.S. Pat. No. 3,674,651 which uses the combination of diphenylamine-benzoquinone .(or hydroquinonemonomethyl ether)-oxygen.

U.S. Pat. No. 4,663,480 discloses that manganese nitrite, i.e. $Mn(NO_2)_2$, effectively inhibits undesired polymerization of ethylenically unsaturated monomers such as unsaturated hydrocarbons, hydrocarboxyl acids and hydrocarboxyl esters. It discloses a process for inhibiting polymerization of a polymerizable ethylenically unsaturated monomer selected from the group consisting of polymerizable ethylenically unsaturated hydrocarbons, polymerizable ethylenically unsaturated acids and polymerizable ethylenically unsaturated esters, which comprises admixing therewith manganese nitrite in an amount effective for inhibiting polymerization, e.g. thermal polymerization, of the monomer. It is further disclosed that, in general, such amount may be for example from about 0.001 to about 0.05 part by weight per 100 parts by weight of the monomer. A composition is also disclosed which is a mixture of the above ethylenically unsaturated monomer and $Mn(NO_2)_2$ in an amount effective for inhibiting thermal polymerization of the monomer.

U.S. Pat. No. 4,021,310 discloses carrying out the distillation for separating or purifying the acrylic acid obtained by the vapor phase catalytic oxidation of propylene or acrolein or acrylic esters derived from the aforesaid acrylic acid, in the presence of (A) at least one compound selected from the group consisting of hydroquinone, hydroquinonemonomethyl ether, cresols, phenols, t-butyl catechol, diphenylamine, phenothiazines, various other compounds described in the patent, and methylene blue;

(B) at least one compound selected from the group consisting of copper dimethyldithiocarbamate, copper diethyldithiocarbamate, copper dibutyldithiocarbamate and copper salicylate; and (C) molecular oxygen.

The '310 patent discloses that some of the compounds of groups (A) and (B), above, are known as polymerization inhibitors of acrylic acid or its esters and that the simultaneous use of these compounds with molecular oxygen is also known. In contrast to these known methods, the '310 patent describes the simultaneous use of the aforesaid three components of groups (A), (B) and (C) in the distillation of acrylic acid or its esters, thereby gaining a synergistic effect.

Thus as noted, polymerizable ethylenically unsaturated monomers such as hydrocarbons, acids and esters undesirably polymerize at various stages of their manufacture, processing, handling, storage and use. A particularly troublesome problem is equipment fouling caused by polymerization in the purification stages of monomer production processes. Polymerization, such as thermal polymerization, during the purification of monomers results in the loss of monomeric material and in loss of production efficiency because the polymer often deposits in or on equipment in contact with the monomers and must be removed at frequent intervals.

As has been discussed above, a wide variety of substances have been proposed for inhibiting uncontrolled polymerization, e.g., thermal polymerization, of the above ethylenically unsaturated monomers. However, the heretofore proposed substances have not been entirely satisfactory. Accordingly, there is a substantial need in the art for improved compositions in which polymerization of such monomers is inhibited during transport and storage as well as during the distillation process for purifying or separating the acrylic monomer.

SUMMARY OF THE INVENTION

A stabilized acrylic monomer composition is provided in which polymerization of the monomer is inhibited during transport and storage as well as during the distillation process for purifying or separating the acrylic monomer. The compositions of the present invention comprise three components: an acrylic monomer (A), phenothiazine (B), and a cyclic amine having at least one hydroxyl group (C).

During transport and storage, components (B) and (C) are present in a polymerization-inhibiting amount. During the distillation process, a fourth essential component, oxygen (D) is added (as set forth in co-pending application Attorney Docket No. 2870, filed herewith), with components (B) and (C) and, during distillation, (B), (C) and (D), being present collectively in a polymerization-inhibiting amount.

Preferably, component (B) is present in an amount of from about 50 to about 1000 ppm, and component (C) is present in an amount of from about 10 to about 500 ppm. During distillation, component (D) is present in a amount of from about 100 to about 10,000 ppm; with the ppm being based on oxygen content. Component (D) may be added as air or molecular oxygen.

DESCRIPTION OF THE INVENTION

A stabilized acrylic monomer composition is provided in which polymerization of the monomer is inhibited during transport and storage as well as during the distillation process for purifying or separating the acrylic monomer. The compositions of the present invention comprise three components: an acrylic monomer (A), phenothiazine (B), and a cyclic amine having at least one hydroxyl group (C). During transport and storage, components (B) and (C) are present in a polymerization-inhibiting amount. During the distillation process, a fourth essential component, oxygen (D) is added, with components (B), (C) and (D) being present collectively in a polymerization-inhibiting amount.

Preferably, component (B) is present in an amount of from about 50 to about 1000 ppm, component (D) is present in an amount of from about 10 to about 500 ppm, and during distillation, component (D) is present in an amount of from about 100 to about 10,000 ppm; with the ppm being based on oxygen content. Component (D) may be added as air or molecular oxygen.

More preferably, component (B) is present in an amount of from about 50 to about 600 ppm, component (C) is present in an amount of from about 10 to about 200 ppm, and during distillation, component (D) is present in an amount of from about 100 to about 1000 ppm. Most preferably, component (B) is present in an amount of from about 50 to about 550 ppm, component (C) is present in an amount of from about 10 to about 100 ppm, and during distillation, component (D) is present in an amount of from about 100 to about 500 ppm.

In one particularly preferred embodiment, component (B) is present in an amount of from about 50 to about 550 ppm, component (C) is present in an amount of from about 10 to about 50 ppm, and during distillation, component (D) is present in an amount of from about 100 to about 400 ppm.

In another particularly preferred embodiment, component (B) is present in an amount of from about 50 to about 200 ppm, component (C) is present in an amount of from about 10 to about 30 ppm, and during distillation, component (D) is present in an amount of from about 100 to about 300 ppm.

The acrylic monomer is selected from the group consisting of acrylic acid, methacrylic acid, alkyl esters of acrylic acid and an alcohol having from one to about 8 carbon atoms, and alkyl esters of methacrylic acid and an alcohol having from one to about 8 carbon atoms or from the group consisting of the acrylic acid esters of alcohols selected from the group consisting of methyl, ethyl, butyl and 2-ethylhexyl alcohol and the methacrylic acid esters of these alcohols. Preferably, the acrylic monomer is acrylic acid.

The cyclic amine having at least one hydroxyl group is preferably Actrene 235 or Actrene 7105, which are solutions of the active ingredient in solvent and are commercially available EXXON Chemical Corporation. The preferred solvents are xylene or dimethyl phthalate. In either of these solvents, the cyclic amine having at least one hydroxyl group is a red solution.

The oxygen may be added as molecular oxygen or as air. Air is preferred. The oxygen, whether molecular or present in air, may be added at any point within the distillation column but is preferably added at the bottom of the distillation column.

The phenothiazine useful in the present invention is commercially available as a yellow solid from a number of sources including Aldrich Chemical Company and ICI Chemical Company and is typically employed at a purity of 99%.

The amounts in which the components (B) and (C) and during distillation, the oxygen (D) are used will vary depending upon various conditions including the monomer and, during distillation, the operating conditions.

The foregoing components (B) and (C) dissolve with relative ease in water or organic solvents that are used in the process of preparing acrylic acid or its esters. Hence, the composition can be made by dissolving them in the acrylic monomer solution. During distillation, the oxygen is typically introduced from the bottom of the distillation column in the gaseous state.

The composition which includes component (D) may be used in the various distillation steps that are carried out in the distillation column for purifying acrylic monomers, for separating acrylic acid from the solvent, for separating such light fractions as acetic acid from acrylic acid, for separating acrylic acid from acrylic esters and alcohol, for separating such light fraction as acrolein from the aqueous solution of acrylic acid, for separating such light fraction as alcohols from acrylic esters and for separating alcohols from raffinate (the aqueous solution of alcohol and acrylic ester.)

The composition is also useful in the various steps that are carried out in the condensation column for acrylic acid and in the esterification reactor.

The compositions of the invention may be stored, handled, and used as monomeric material in polymerization processes, and otherwise, with continuing inhibition of thermal polymerization.

The present invention is further illustrated by the following non-limiting examples. All parts, percentages and other amounts given throughout this disclosure are by weight unless otherwise indicated.

EXAMPLES

In the following examples, "PTZ" represents phenothiazine; and 7105 is a cyclic amine having at least one hydroxyl group which is available from EXXON Chemical Company as ACTRENE 7105 and which, as used, was a solution of the active ingredient in dimethyl phthalate.

The plant process was simulated in the examples using standard laboratory glassware.

A 250 ml round bottom flask referred to as the "boiling flask" was placed on a stir plate and fitted with a heating mantel, a magnetic stirrer, a first thermometer and two lines.

The first thermometer was used to measure the temperature of the liquid acrylic acid in the boiling flask. This temperature was typically 100° C.

The first line entered the flask in the middle of one side and led through first and second valves to a 500 ml round bottom flask which was otherwise closed to the atmosphere. This was the "bottoms recovery flask".

The second line led off a side of the neck of the flask and along this line was a vacuum gauge and then an air addition inlet through which atmospheric air was introduced. The second line then branched after a valve, leading along one branch into the first line above the 500 ml round bottom flask and below the second valve on that line, and along the other branch through a valve into a cold trap. The cold trap was connected to a Hg Manometer from which a line led to a vacuum pump. Intermediate the Manometer and pump was a bleed valve for vacuum control to keep the system pressure constant. The vacuum pressure was typically 125 mm Hg as measured at the manometer.

The neck of the 250 ml round bottom flask was fitted to a distillation column comprising a 4×1 in. packed column which in turn was connected to a 3×1 in. reflux adapter, which in turn was connected to a 2×1 in. packed column which was in turn connected to a 3×1 in. feed adapter, which in turn was connected to a 13×1 in. packed column, which was fitted at its upper end with a second thermometer.

The 3×1 in. reflux adapter was used to feed acrylic acid inhibited with PTZ from a first feed reservoir. The flow rate was approximately 5 ml/min.

The 3×1 in. feed adapter was used to feed acrylic acid inhibited with phenothiazine or, when Actrene 7105 was employed, a combination of the three. The flow rate was approximately 0.5 ml/min.

At the flow rates used, about 4 ml/min distilled overhead and 1.5 ml/min went to the bottoms recovery flask.

The second thermometer was used to measure the temperature of the acrylic acid vapor at the top of the column. This temperature was typically 80° C.

The packing was high efficiency 316 stainless steel packing obtained from Scientific Development Company.

The 13×1 in. packed column was connected along a side adjacent its upper end to a reflux condenser with a coolant outlet adjacent the upper end of the packed column and a coolant inlet at its other end. This reflux condenser was in turn connected through a line to a second reflux condenser with a coolant outlet adjacent the first condenser and a coolant inlet at its other end.

The second reflux condenser was in turn connected to a graduated column having a line adjacent the connection which branched at a first valve and led from the valve to the other end of the graduated column through a second valve along one branch and along the other branch to the second branch of the line from the air addition point between the valve in that line nearest the cold trap and the cold trap itself.

The other end of the graduated column was connected to a 500 ml round bottom flask.

The experimental procedure was to start the acrylic acid flow to the column through the 3×1 in. reflux adapter with the vacuum on and the heat off. When the flows had been set and the boiling flask was full, the heating mantle was turned on. The length of the experiment was measured from the time that the heat was turned on until the experiment ceased. The stopping point of the experiment occurred when sufficient polymer had formed in the column such that the column flooded or a large increase in system pressure was measured.

In this manner, experiments were run showing that the combination of components (A), (B) and (C) significantly improved the experiment lifetime as compared to the runs without one of the three components.

| EX. NO. | INHIBITOR | AMOUNT (PPM) | # OF RUNS | RUN TIME (HRS) | RESIDUE IN BOILING POT (GRAMS) | VAPOR PHASE |
|---|---|---|---|---|---|---|
| 1 | PTZ<br>NO AIR<br>NO 7105 | 100 | 6 | 0.95 | 3.1 | COLUMN COMPLETELY PLUGGED |
| 2 | PTZ<br>AIR<br>NO 7105 | 100 | 5 | 1.0 | 3.6 | COLUMN COMPLETELY PLUGGED |
| 3 | 7105<br>PTZ<br>NO AIR | 800<br>100 | 1 | 2.5 | 0.0 | TOP SECTION PLUGGED |
| 4 | 7105<br>PTZ<br>NO AIR | 400<br>100 |  | 1.2 | 0.0 | TOP SECTION PLUGGED |
| 5 | 7105<br>PTZ<br>NO AIR | 400<br>100 | 1 | 5.5 | 0.0 | NO POLYMER FORMED |
| 6 | 7105<br>PTZ<br>NO AIR | 200<br>100 | 1 | 7.0 | 0.0 | SMALL AMOUNT OF POLYMER FORMED |
| 7 | 7105<br>AIR<br>NO PTZ | 100<br>200 | 1 | 2.5 | 3.4 | TOP SECTION PLUGGED |
| 8 | 7105<br>PTZ<br>NO AIR | 100<br>100 | 2 | 3.4 | 0.0 | COLUMN PLUGGED |
| 9 | 7105<br>AIR<br>PTZ | 400<br>200<br>100 | 1 | 7.0 | 0.0 | NO POLYMER FORMED |
| 10 | 7105 | 100 | 1 | 7.0 | 0.0 | NO POLYMER |

-continued

| EX. NO. | INHIB- ITOR | AMOUNT (PPM) | # OF RUNS | RUN TIME (HRS) | RESIDUE IN BOILING POT (GRAMS) | VAPOR PHASE |
| --- | --- | --- | --- | --- | --- | --- |
|  | AIR | 200 |  |  |  | FORMED |
|  | PTZ | 100 |  |  |  |  |
| 11 | 7105 | 50 | 2 | 7.0 | 0.0 | NO POLYMER FORMED |
|  | AIR | 200 |  |  |  |  |
|  | PTZ | 100 |  |  |  |  |
| 12 | 7105 | 25 | 1 | 7.0 | 0.0 | NO POLYMER FORMED |
|  | AIR | 200 |  |  |  |  |
|  | PTZ | 100 |  |  |  |  |
| 13 | 7105 | 13 | 2 | 7.0 | 1.9 | NO POLYMER FORMED |
|  | AIR | 200 |  |  |  |  |
|  | PTZ | 100 |  |  |  |  |
| 14 | 7105 | 25 | 2 | 12.5 | 0.9 | EXTENSIVE POLYMER |
|  | AIR | 200 |  |  |  |  |
|  | PTZ | 100 |  |  |  |  |

NOTES:
1. Examples 1 through 8 are comparative examples where one or two of components (B), (C) and (D) are missing.
2. Example 2: the amount of air added was not measured.
3. Examples 5 through 14 are liquid phase evaluations where components (B), (C) and (D) are present.
4. Example 14 formed polymer only after an extremely long run and while in excess of commercially acceptable run times, is presented to demonstrate the inhibiting effect of the combination of components in the present invention.

BEST MODE CONTEMPLATED

The best mode contemplated for carrying out the present invention has been set forth in the above description, for example, by way of setting forth preferred materials and operating conditions, including but not limited to preferred ranges and values of amounts and other non-obvious variables material to successfully practicing the invention in the best way contemplated at the time of executing this patent application.

It is understood that the foregoing detailed description is given by way of illustration and that many modifications may be made therein without departing from the spirit or scope of the present invention.

We claim:

1. A composition comprising a mixture of (A) an acrylic monomer and a polymerization-inhibiting amount of a combination of (B) phenothiazine, and (C) a cyclic amine having at least one hydroxyl group.

2. The composition of claim 1 wherein component (B) is present in an amount of from about 50 to about 1000 ppm, and component (C) is present in an amount of from about 10 to about 500 ppm.

3. The composition of claim 2 wherein component (B) is present in an amount of from about 50 to about 600 ppm.

4. The composition of claim 2 wherein component (C) is present in an amount of from about 10 to about 200 ppm.

5. The composition of claim 1 wherein the acrylic monomer is selected from the group consisting of acrylic acid, methacrylic acid, alkyl esters of acrylic acid and an alcohol having from on to about 8 carbon atoms and alkyl esters of methacrylic acid and an alcohol having from one to about 8 carbon atoms.

6. The composition of claim 1 wherein the acrylic monomer is selected from the group consisting of the acrylic acid esters of alcohols selected from the group consisting of methyl, ethyl, butyl and 2-ethylhexyl alcohol and the methacrylic acid esters of these alcohols.

7. The composition of claim 1 wherein the acrylic monomer is acrylic acid.

8. The composition of claim 1 in which component (C) is Actrene 7105.

9. A composition comprising a mixture of (A) an acrylic monomer and a polymerization-inhibiting amount of a combination of (B) phenothiazine, and (C) a cyclic amine having at least one hydroxyl group, wherein component (A) is selected from the group consisting of acrylic acid, methacrylic acid, alkyl esters of acrylic acid and an alcohol having from one to about 8 carbon atoms and alkyl esters of methacrylic acid and an alcohol having from one to about 8 carbon atoms, or component (A) is selected from the group consisting of the acrylic acid esters of alcohols selected from the group consisting of methyl, ethyl, butyl and 2-ethylhexyl alcohol and the methacrylic acid esters of these alcohols, component (B) is present in an amount of from about 50 to about 550 ppm, and component (C) is present in an amount of from about 10 to about 100 ppm.

10. The composition of claim 9, in which component (C) is present in an amount of from about 10 to about 50 ppm.

11. The composition of claim 9, in which component (B) is present in an amount of from about 50 to about 200 ppm, and component (C) is present in an amount of from about 10 to about 30 ppm.

12. The composition of claim 9, in which component (C) is Actrene 7105.

* * * * *